United States Patent [19]

Hill

[11] 4,366,574
[45] Dec. 28, 1982

[54] SHADOWGRAPHIC SLIT SCANNER WITH VIDEO DISPLAY

[75] Inventor: Edwin R. Hill, Chardon, Ohio

[73] Assignee: Technicare Corporation, Solon, Ohio

[21] Appl. No.: 202,504

[22] Filed: Oct. 31, 1980

[51] Int. Cl.³ ............................................. G03B 41/16
[52] U.S. Cl. ....................................... 378/99; 378/146
[58] Field of Search .......................... 250/505, 416 TV

[56] References Cited

U.S. PATENT DOCUMENTS

| | | |
|---|---|---|
| 2,730,566 | 1/1956 | Bartow et al. |
| 2,825,817 | 3/1958 | North |
| 3,790,799 | 2/1974 | Stein et al. |
| 4,048,505 | 9/1977 | Hounsfield |
| 4,096,391 | 6/1978 | Barnes ................................ 250/505 |
| 4,097,748 | 6/1978 | Monvoisin ........................... 250/505 |
| 4,119,841 | 10/1978 | Jantsch et al. |
| 4,179,100 | 12/1979 | Sashin ........................... 250/416 TV |

OTHER PUBLICATIONS

A High Resolution Solid State Charge Coupled Device (CCD) Space Borne Earth Imager, Hirschberg, *SPIE*, vol. 143, "Applications of Electronic Imaging Systems" (1978).
Reduction of Scatter in Diagnostic Radiology by Means of a Scanning Multiple Slit Assembly, Barnes et al., *Radiology*, Sep. 1976 (pp. 691-694).
The Design and Performance of a Scanning Multiple Slit Assembly, Barnes and Brezovich, *Med. Phys.* 6(3), May/Jun. 1979 (pp. 197-204).

*Primary Examiner*—Craig E. Church

*Attorney, Agent, or Firm*—Michael A. Kaufman

[57] ABSTRACT

A shadowgraphic scanner for producing electronic two-dimensional shadowgraphic images of an examined region of a patient. A source of radiation produces a generally planar beam of radiation which is scanned along the examined region. A two-dimensional array of radiation detectors fixed relative to the source of radiation, but movable in unison therewith relative to the patient. The two-dimensional array of radiation detectors includes a plurality of columns of detectors arranged transverse to the direction in which the beam of radiation is scanned. A first collimator is placed between the source and the patient and a second collimator is placed between the patient and the array of detectors. Both collimators are fixed relative to the source and the detectors and are configured and dimensioned to permit passage therethrough of a beam of radiation of a cross section which corresponds in size to the array of detectors to irradiate the entire array, as the patient is being scanned. Each column of detectors sequentially detects radiation passing through the same section so that a detector from each column contributes sequentially to each section of the examined region. An analog memory cyclically sums the output of each of the columns of radiation detectors in a corresponding plurality of columns of memory units. When a column of memory units has summed the output from each of the columns of detectors, the sum is transferred to an image memory, the memory units in the column zeroed, and the cycle repeated until the entire region of interest is scanned. The data stored in the image memory is displayed on a video monitor.

9 Claims, 2 Drawing Figures

SHADOWGRAPHIC SLIT SCANNER WITH VIDEO DISPLAY

BACKGROUND OF THE INVENTION

This application pertains to the art of shadowgraphic imaging and more particularly to the art of electronic shadowgraphic imaging. The invention is particularly applicable to shadowgraphic scanners which display a shadowgraphic image on a video monitor and will be described with particular reference thereto. It will be appreciated, however, that the invention has broader applications such as to scanners which electronically produce printed images, CRT displays, and other representations of shadowgraphic data.

One of the earliest applications of medical X-ray technology was the X-ray shadowgraph. An X-ray source was placed in front of the patient and photographic film placed on the opposite side of the patient. The X-ray source was actuated for a sufficient duration to expose the photographic film. With advances in electronics, improvements soon were made upon X-ray shadowgraphic photography.

For example, as shown by U.S. Pat. No. 2,730,566 to Bartow et al., issued Jan. 10, 1956, it was found that one could produce shadowgraphic images electronically. In the Bartow device, a beam of X-rays is swept through the patient onto an electronic X-ray detector. By sweeping the beam in a pattern which correlates to the electron beam sweep pattern, shadowgraphic images could be produced on a cathode ray tube. Others soon discovered that video displays could be produced from the data collected by sweeping an X-ray beam through the patient. See, for example, U.S. Pat. No. 2,825,817 to North, issued Mar. 4, 1958.

It was also learned that low energy radiation was scattered in the patient's body. Scattered radiation which strikes the film or detector degrades the shadowgraphic image. In film systems, it was found that the amount of scatter could be reduced by placing a beam defining slit between the X-ray source and the patient and another beam defining slit between the patient and the X-ray film. Rather than exposing the entire piece of film at the same time, the two slits were moved in unison such that a narrow band of radiation was swept across the film. Such shadowgraphic scanners with beam defining slits are commonly called slit scanners. It was later found that the use of a plurality of parallel spaced slits allows shadowgraphic images to be produced more quickly. See, for example, U.S. Pat. No. 4,096,391 to Barnes, issued June 20, 1978, and U.S. Pat. No. 4,097,748 to Monvoisin, issued June 27, 1978.

One of the problems with shadowgraphic imaging devices that employ moving slits of radiation is the large energy requirements to which the X-ray tubes are subjected. The amount of radiation produced by an X-ray tube is independent of any beam defining slit with which it may be used. Thus, even if only a relatively small area of the patient is permitted to be irradiated in a scan, the X-ray tube still requires the same amount of energy as it would need without the slit. Moreover, the same exposure time is required to expose a small slit-shaped area as a large area. However, since the number of exposures required to scan a given area is increased if a slit is used, the X-ray tube must be actuated for a proportionately longer duration. By way of example, to form a square image with a slit that is sixteen times as long as it is wide, the slit must be placed at sixteen sequential positions and retained at each such position for an exposure duration. This requires the X-ray tube to be operated for a duration sixteen times as long as it would to expose or image the entire area in one exposure, i.e., without a slit.

Moreover, X-ray tubes are only able to operate at their maximum energy or watt-second rating for a relatively short duration without overheating and hence damaging their anodes. To avoid damaging or melting the anode of the X-ray tube during the extended scanning time required by a slit, the X-ray tube must be operated at a lower power or wattage. However, lowering the power of the X-ray tube, similarly lowers the intensity of radiation produced. To compensate, the slit shaped beam of radiation must dwell in a location for a correspondingly longer duration.

When video medical images are produced today, it is common to divide the examined area of the patient into a matrix of 512 by 512 units or pixels. This number is selected because conventional video monitors have 512 scan lines per frame. Sweeping a slit shaped beam of radiation that has a width of only one 512th of the length of the area to be imaged greatly aggravates the X-ray tube energy problems and extended scanning time problems referenced above. Even if several parallel spaced slits are scanned simultaneously, the X-ray tube would still be called upon to supply many times more power and operate many times longer than practicable.

The present invention contemplates a new and improved shadowgraphic slit scanner which overcomes the above-referenced problems and others by balancing the noted constraints on time of scanning and the power of X-ray tubes in combination with a relatively wide slit to simultaneously expose a plurality of radiation detectors. The inventive scanner further provides electronic or video shadowgraphic images which are substantially free of scatter degradation.

SUMMARY OF THE INVENTION

In accordance with the present invention, there is provided a shadowgraphic scanner and method of shadowgraphic scanning which produce electronic representations of shadowgraphic projections through a patient or other examined object with minimal scanner degradation, with relatively low intensities of radiation, and with a relatively fast speed.

In accordance with a preferred embodiment of the present invention, there is provided a shadowgraphic slit scanner for producing electronic two-dimensional shadowgraphic representations of an examined object. The scanner includes means for supporting the object to be examined, a source of penetrating radiation disposed to irradiate at least part of the support means, and a two-dimensional array of radiation detectors disposed opposite the support means to receive radiation from the source after the radiation traverses the support means. The array of radiation detectors is arranged in a plurality of columns in fixed orientation relative to the source for receiving radiation from the source after the radiation passes through sections of the portion of interest of the patient. The scanner further comprises means for moving both the source and detectors relative to the patient such that each column of the detectors of the array passes sequentially over the same section of the patient. Disposed between the source and the array of detectors is at least one collimator arranged in fixed relation thereto for permitting passage therethrough of a beam of radiation of a width corresponding to a plurality of the columns of detectors. The scanner further comprises means for synchronously accumulating positionally dependent radiation information from the array of detectors as the array is moved relative to the region of interest of the patient being examined. Connected with the detector array is an electronic means for converting electric signals from the detectors which indicate the intensity of received radiation into the representation of the shadowgraphic image.

DESCRIPTION OF THE DRAWINGS

The figures are illustrative of a preferred embodiment of the present invention.

DESCRIPTION OF THE PREFERRED EMBODIMENT

Figure 1:
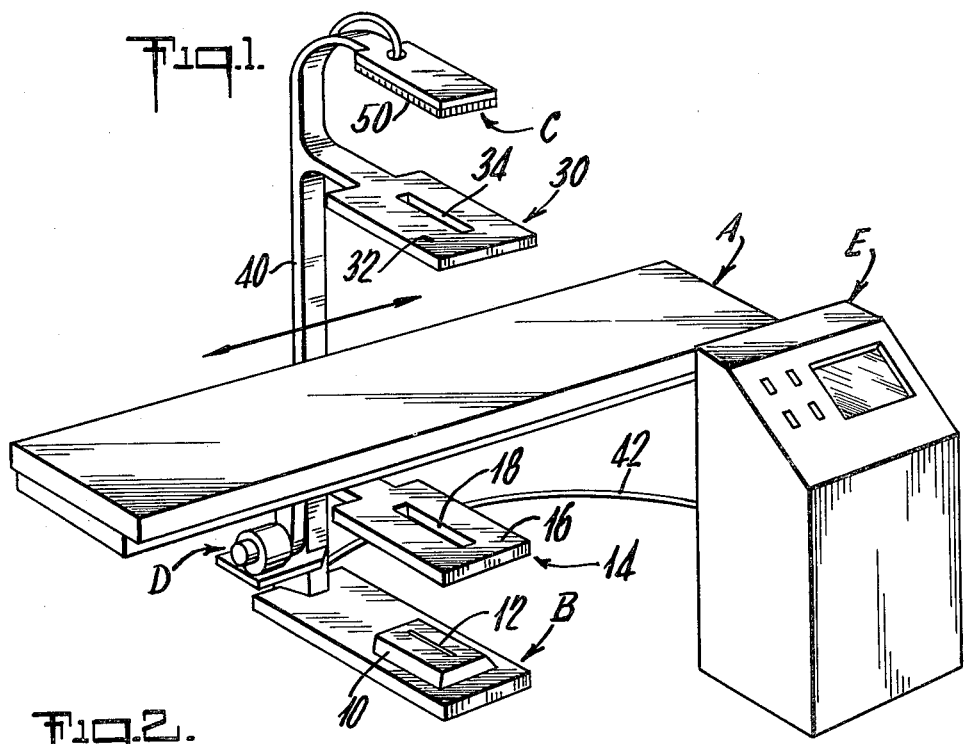
FIG. 1 illustrates an apparatus for scanning an examined object with radiation in accordance with the present invention.

With reference to FIG. 1, a support means A such as a patient table is provided for supporting the object which is to be examined. Beneath the support means A is a penetrating radiation source B, for producing a generally planar beam of radiation. A beam of radiation is wider than it is thick. The ratio of these two dimensions is denoted the aspect ratio. The radiation source B is arranged to traverse a relatively long, thin part of the support means A with the beam of radiation. A two-dimensional array of radiation detectors C is disposed above the support means A and is arranged to receive radiation emitted by the source B after traversing support means A. A motor D causes relative movement between the support means A and the beam of radiation emitted by source B. More specifically, longitudinal relative movement is caused between the support means A and at least one of the radiation source B and the detector array C. Thus, the thin beam of radiation is swept longitudinally along the support means A.

Each of the detectors in the array C produces analog output signals which vary in amplitude with the intensity of the received radiation. An electronic control means E converts electrical output signals into an electronic two-dimensional representation of a shadowgraphic projection of the examined object.

Referring now to FIG. 1 in greater detail, support means A is a patient table upon which a patient can be supported in a supine position for examination. The patient table is constructed of a material such as fiberglass, aluminum, wood, or the like which readily transmits radiation. The patient table is mounted on a track (not shown) along which it is longitudinally slidable. The patient table, track, mounting and moving structure, and the like are constructed to cause no nonuniform shadow in the beam of radiation.

The source of penetrating radiation B is an X-ray tube or other source of x, gamma or other penetrating radiation disposed in radiation opaque housing 10. A lateral slit 12 in the top of the housing 10 permits the generally planar beam of radiation to be projected upward. Above the opaque housing 10 there is provided a first collimator or means 14 for defining the sectional dimensions of the X-ray beam. The first collimator 14 comprises a radiation opaque shield 16 which has a lateral radiation transmissive portion 18 oriented generally parallel to lateral slit 12. The radiation transmissive portion 18 is preferably an aperture, but may be a strip of plastic, aluminum or other filtering material. The radiation defining slit 18 is elongated in the transverse direction and narrow in the longitudinal direction.

Disposed in alignment with slits 12 and 18 is the array of radiation detectors C. The dimensions of slit 18 and the distance to detectors C are chosen to define a beam of radiation which dimensionally corresponds to and hence irradiates the entire radiation sensitive face of the array of radiation detectors. If the cross section of the beam of radiation is not sufficient to irradiate the entire array of detectors, a portion of the image would be lost. Conversely, if the beam of radiation is larger than would be required to irradiate the cross section of the array of detectors C, then the examined object would be subject to excess radiation since only that portion of the beam which impacts on the detectors contributes to the shadowgraphic image. Excess radiation would increase the amount of scatter degradation to the image.

To reduce degradation of the resultant image from scattered radiation caused, for example, by the patient table A and the patient, a scatter radiation shielding means 30 or second collimator is provided between the patient and the array of radiation detectors C. The radiation scatter shield 30 includes a radiation opaque shield 32 which has a lateral radiation transmissive portion comparable to slit 18 in opaque shield 16. The radiation transmissive portion 34 is preferably an aperture, but alternatively may be a strip of plastic, aluminum or other filtering material. The dimensions of slit 34 are designed to correspond to the cross section of the beam of radiation at the distance from the source of radiation B where radiation shield 30 is located. The slit 34 permits passage therethrough of radiation originating from the source B on its course to the face of the array of radiation detectors C. The opaque shield 32 blocks scattered radiation from impinging on the detector array C.

A stand or frame 40 is provided for supporting in alignment the radiation source B, the beam defining means 14, the scatter radiation shielding means 30, and the array of radiation detectors C. The motor D causes relative movement between the patient table A and radiation source B by moving the patient table A longitudinally relative to the frame 40. For this purpose, motor 40 is preferably provided with a rotating gear which engages a rack gear, both not shown, along one edge of the undersurface of the patient table. Alternately, the motor causes the source of radiation and the radiation detector to move in unison relative to a stationary patient table. The frame 40 preferably moves linearly. Alternatively, it may be arranged to pivot to cause the relative movement. If the frame 40 is pivoted, one of the source of radiation B and the detector array C is moved relative to the patient table with the other held stationary. An electric cable 42 connects the detector array C and the X-ray tube with the electronic control means E.

Figure 2:
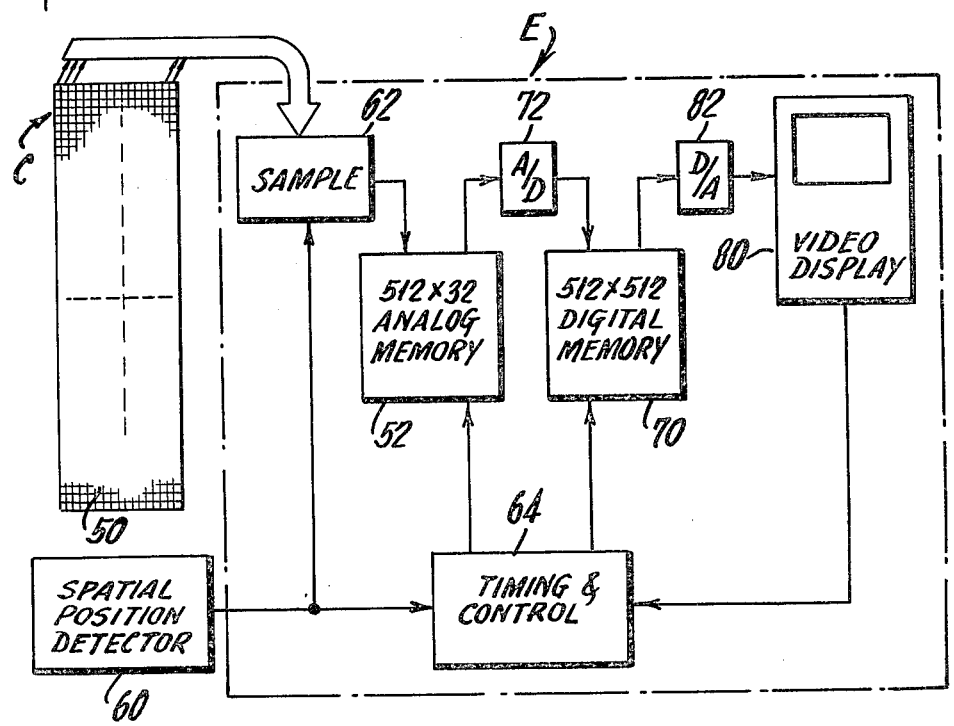
FIG. 2 illustrates a preferred embodiment of the electronic circuitry for converting the radiation detected by the detector array in FIG. 1 to a video image.

With reference to FIG. 2, the detector array C is a self-scanned solid state charge coupled device-photodiode array. Specific to the preferred embodiment, the detector array includes a 512 by 32 matrix of photodiodes 50 arranged in 32 parallel columns of 512 detectors extending in the transverse direction. Each photodiode converts the radiation it receives into an electrical output signal whose magnitude varies with the intensity of received radiation. Thus, a relatively radiation opaque substance, such as bone, disposed between the source of radiation and one of the photodiodes, results in a relatively low level of radiation intensity received by that photodiode and hence that photodiode produces an electrical signal with a relatively small amplitude. Conversely, if a portion of the examined object which is relatively radiation transmissive, such as fat tissue, is disposed between the source of radiation and one of the photodiodes, radiation of a relatively high intensity is received and an electrical signal with a relatively large amplitude is produced.

The photodiode array 50 includes 32 columns of photodiodes extending in the transverse direction and 512 rows of photodiodes extending in the longitudinal direction. Each photodiode is identifiable in terms of the row and column in which it is disposed. An analog memory 52 is connected to the detector array 50. The analog memory 52 consists of a plurality of storage units, such as charged coupled devices, for storing analog signals. In the preferred embodiment, a 512 by 32 matrix array of storage units is provided. In operation, as a photodiode is sampled, its electrical output signal causes an electrical charge to be stored in a corresponding storage unit or charge coupled device. Each time a charge coupled device samples a photodiode, the additional electrical output signal sensed increases the electrical charge which is stored by that device. In this manner, the storage units sum successive stored output signals until they are cleared or zeroed.

A spatial position detector 60 monitors the relative movement between the support means A and the beam of radiation. The spatial position detector provides a pulse corresponding to each incremental amount of relative movement. A preferred incremental amount of relative movement is the center to center spacing of the columns of photodiodes. Thus each time the columns of photodiodes are shifted a distance equivalent to the width of one column, there is one incremental amount of relative movement. For example, after one incremental amount of relative movement, the second column of photodiodes is receiving radiation which has traversed the same region of the examined object that the first column of photodiodes received before that incremental movement. Simultaneously, the remaining columns of photodiodes are receiving radiation from remaining sections of the patient being radiated. After a second incremental amount of relative movement, the third column of photodiodes is receiving the radiation which has traversed this same region of the examined object and so forth. Though this relative movement is described as incremental for the purpose of monitoring the relative location of a section of the patient and the beam of radiation, the movement is preferably continuous.

A sampling means 62 is provided for sampling the photodiodes after each incremental movement to store their analog outputs in corresponding storage units of the analog memory 52. A timing and control means 64 alters the addresses in the analog memory means 52 by one column after each incremental movement. That is, each column of storage units is caused sequentially to store the output signal from the photodiodes in each of the 32 columns. In this manner, the first column of charge coupled devices stores electric signals from the first column of photodiodes the first time the photodiode array is sample. The second time the photodiode array is sampled, the electric signals from the second column of photodiodes is stored in the first column of charge coupled devices. After the third incremental amount of movement, the electric signals from the third column of photodiodes are stored in the first column of charge coupled devices, and so forth. Because the sequential storing of analog outputs is synchronized with the incremental amounts of relative movement, the analog outputs stored in each storage unit correspond to the intensity of radiation traversing the examined object along the same path.

In other words, as the X-ray beam is swept through a section of the patient, each of the 32 columns of detectors is above the same slice of that section of the patient for an equal time duration. During that 1/32 time duration, each column of detectors senses radiation passing through that slice of the patient and transmits an electronic signal which contributes sequentially to information from that slice. Thus, every one of the 32 columns in the analog memory 52 is a composite of signals received sequentially from each of the 32 columns of detectors; however, every column of the analog memory 52 relates only to a single positional slice of the patient for every 32 increments of movement.

After the last column of photodiodes is positioned above a given sectional slice of the patient, no additional columns of photodiodes will sense radiation through that region. At that point, the electric signals stored in a column of the storage units corresponding to a slice as represented by the sum of thirty-two contributions, one from each column of detectors. At that time, the timing and control means 64 causes the electric signals stored in that column to be transferred to a corresponding column of an image memory 70. When the stored signals have been moved to the image memory 70, the column of storage units are reset or zeroed. The zeroed column is then reassigned to a region of the examined object thirty-two incremental amounts ahead, i.e. the width of the X-ray beam. Radiation is then directed through this slice of the patient for the first time by the leading column of photodiodes. Sequentially, the remaining columns of photodiodes will receive radiation transmitted through this section and their outputs will be summed into this column of storage units.

In the preferred embodiment, the image memory 70 is a digital memory. Accordingly, an analog to digital converter 72 is provided for converting the columns of analog data from analog memory 52 into digital data. In the preferred embodiment, the image memory 70 is a 512×512 array of digital memory units. After each incremental amount of relative movement, the timing and control means 64 cyclically causes the stored signals from one of the columns of the analog memory 52 to be stored in sequential columns of the digital image memory 70. When the image memory 70 is full, the data stored therein is a representation of a shadowgraphic projection through at least a portion of the examined object.

The representation can be visually displayed on a video display 80 or other display means. A digital to analog converter 82 converts digital data retrieved from the image memory 70 into analog form for display on the video display 80. The video display 80 is connected with the timing and control means 64 to synchronize the retrieval of data from the image memory 70 with the sweep of the video beam. The rows of data from the image memory 70 are retrieved by the video display 80 to be displayed as horizontal sweep lines. The photodiode array 50, the sampling means 62, and the analog memory 52 are available as an integral commercially manufactured device. For example, a series of Reticon RL512SFX self scanned photodiode arrays (SSPA) can be combined to form the 512×32 array.

The invention has been described with reference to the preferred embodiment. Numerous alternative embodiments are contemplated by the present invention. For example, the radiation source may be arranged to irradiate a plurality of detector columns or arrays which are arranged parallel to each other but spatially separated. This construction would enable the scanner to collect data concerning several parts of the examined object simultaneously. Further, the stored data may be processed or supplemented to improve the quality or utility of the image.

I claim:

1. A slit scanner for producing an electronic two-dimensional shadowgraphic image of a region of an examined object, such as a patient, which comprises:
   (a) a source of penetrating radiation for directing a beam of radiation through a portion of interest of the object;
   (b) an array of radiation detectors, arranged in a plurality of columns and in fixed orientation relative to the source, for receiving radiation from the source after the radiation passes through the patient;
   (c) at least one collimator disposed between the source and the array of radiation detectors, the collimator permitting passage through it of a beam of radiation substantially corresponding in cross section to the sensitive face of the detector array;
   (d) means for causing relative motion between the object and the detector array such that each column of the detectors of the array sequentially detecting a portion of the beam that has penetrated a particular section of the region of the object being examined;
   (e) means for storing and accumulating electrical signals from the columns of the array in synchronism with relative motion between the object and the array such that signals from different columns representative of radiation transmission through the same respective particular sections of the object are added together; and
   (f) means for displaying a shadowgraph image of the region of the object.

2. A slit scanner according to claim 1 wherein the array comprises columns of photodiodes which are scanned, the means for storing and accumulating electrical signals causing the signals obtained from each scan of a column of the array to be added to the signal obtained from a previous scan of an adjacent column.

3. A slit scanner according to claims 1 or 2, the scanner further comprising means for supporting a patient between the source and the array of radiation detectors, and a second collimator, the first collimator being disposed between the source of penetrating radiation and the patient support means and the second collimator being disposed in alignment with the first collimator and between the patient support means and the array of radiation detectors, the collimators and patient support means being the only apparatus other than the patient positioned between the source of penetrating radiation and the array of radiation detectors.

4. A slit scanner according to claims 1 or 2, the scanner further comprising a spatial position detector for monitoring the movement of the object and the detectors relative to one another, an addressable memory, the addressable memory being supplied with electrical signals from the columns of the array of radiation detectors, and timing and control means for altering the addresses in the memory to which the electrical signals from each of the columns are sent, the altering of addresses being in response to changes in the position of the object relative to the source or detectors as sensed by the spatial position detector.

5. A slit scanner according to claim 4 wherein the addressable memory is an analog memory.

6. A slit scanner according to claim 5 which further comprises a digital memory, and an analog-to-digital converter interconnecting the analog memory and the digital memory, the accumulated electrical signals for the particular section of the region of the object being examined being transferred from the analog memory and through the converter to the digital memory, and means for zeroing the storage locations of the analog memory from which the accumulated electrical signals are transferred.

7. A method of forming a representation of a shadowgraphic image comprising:
   (a) irradiating an object with a beam of penetrating radiation that traverses the object;
   (b) detecting the intensity of the beam of radiation which has traversed the object with a plurality of columns of detectors, each detector producing an output signal that is proportional to the intensity of the detected radiation;
   (c) storing the output signals from each column of detectors in each of a plurality of columns or groups of storage units;
   (d) causing an incremental amount of relative movement between the object and the plurality of columns; and
   (e) during the irradiation, repeating steps (b), (c), and (d), the respective columns or groups of storage units during each repetition storing output signals from a column of detectors other than the column of detectors the output signals of which had been stored prior to the previous incremental amount of relative movement.

8. A method according to claim 7 which further comprises transferring stored signals in a column or group of storage units to an image memory after the column or group of storage units has accumulated electrical signals obtained from each of the columns of the array of detectors.

9. A method according to claim 8 which further comprises the step of zeroing the storage units from which the accumulated electrical signals have been transferred to the image memory after such transfer, and again allowing electrical signals to accumulate in the zeroed storage units such that signals from different columns representative of radiation transmission through the same respective particular sections of the object are added together; and
   (f) displaying a shadowgraph image of the object.

* * * * *

UNITED STATES PATENT AND TRADEMARK OFFICE
CERTIFICATE OF CORRECTION

PATENT NO. : 4,366,574

DATED : December 28, 1982

INVENTOR(S) : Edwin R. Hill

It is certified that error appears in the above—identified patent and that said Letters Patent is hereby corrected as shown below:

Claim 7 should read as follows:

7. A method of forming a representation of a shadowgraphic image comprising:

(a) irradiating an object with a beam of penetrating radiation that traverses the object;

(b) detecting the intensity of the beam of radiation which has traversed the object with a plurality of columns of detectors, each detector producing an output signal that is proportional to the intensity of the detected radiation;

(c) storing the output signals from each column of detectors in each of a plurality of columns or groups of storage units;

(d) causing an incremental amount of relative movement between the object and the plurality of columns; and (e) during the irradiation, repeating steps (b), (c), and (d), the respective columns or groups of storage units during each repetition storing output signals from a column of detectors other than the column of detectors the output signals of which had been stored prior to the previous incremental amount of relative movement such that signals from different columns representative of radiation transmission through the same respective particular sections of the object are added together; and (f) displaying a shadowgraph image of the object.

UNITED STATES PATENT AND TRADEMARK OFFICE
CERTIFICATE OF CORRECTION

PATENT NO. : 4,366,574

DATED : December 28, 1982

INVENTOR(S) : Edwin R. Hill

It is certified that error appears in the above—identified patent and that said Letters Patent is hereby corrected as shown below:

Claim 9 should read as follows:

9. A method according to claim 8 which further comprises the step of zeroing the storage units from which the accumulated electrical signals have been transferred to the image memory after such transfer, and again allowing electrical signals to accumulate in the zeroed storage units.

Signed and Sealed this

Thirteenth Day of December 1983

[SEAL]

*Attest:*

GERALD J. MOSSINGHOFF

*Attesting Officer*  *Commissioner of Patents and Trademarks*